(12) United States Patent
Ficheux et al.

(10) Patent No.: US 8,298,427 B2
(45) Date of Patent: Oct. 30, 2012

(54) APPARATUS FOR EXTRACORPOREAL BLOOD TREATMENT AND METHOD FOR MANAGING SUCH AN APPARATUS

(75) Inventors: Alain Ficheux, Grabels (FR); Angel Argiles Ciscart, Saint Gely du Fesc (FR)

(73) Assignee: RD Nephrologie, Montpellier (FR)

( * ) Notice: Subject to any disclaimer, the term of this patent is extended or adjusted under 35 U.S.C. 154(b) by 8 days.

(21) Appl. No.: 13/122,878

(22) PCT Filed: Sep. 24, 2009

(86) PCT No.: PCT/FR2009/051812
§ 371 (c)(1),
(2), (4) Date: Apr. 6, 2011

(87) PCT Pub. No.: WO2010/040927
PCT Pub. Date: Apr. 15, 2010

(65) Prior Publication Data
US 2011/0240555 A1    Oct. 6, 2011

(30) Foreign Application Priority Data
Oct. 6, 2008   (FR) ...................... 08 56758

(51) Int. Cl.
*B01D 61/32* (2006.01)
*B01D 61/24* (2006.01)
*B01D 61/30* (2006.01)
*A61M 1/34* (2006.01)

(52) U.S. Cl. ........ 210/650; 210/645; 210/646; 210/739; 210/741; 210/85; 210/87; 210/90; 210/97; 210/102; 210/103; 210/109; 210/134; 210/143; 210/252; 210/257.2; 210/258; 210/321.6; 210/321.65; 604/4.01; 604/5.01; 604/6.09; 604/6.11; 604/28

(58) Field of Classification Search .................. 210/637, 210/645, 646, 650, 739, 741, 85, 87, 90, 210/97, 102, 103, 109, 134, 143, 252, 257.2, 210/258, 321.6, 321.65; 604/4.01, 5.01, 604/6.09, 6.11, 28
See application file for complete search history.

(56) References Cited

U.S. PATENT DOCUMENTS

| 4,661,246 A | 4/1987 | Ash |
| 4,683,053 A | 7/1987 | Polaschegg |
| 6,767,333 B1 | 7/2004 | Müller et al. |
| 2008/0215247 A1 | 9/2008 | Tonelli et al. |

OTHER PUBLICATIONS

French Search Report in the corresponding priority application FR 0856758.
English translation of International Search report in corresponding International Application No. PCT/FR2009/051812.

*Primary Examiner* — John Kim
(74) *Attorney, Agent, or Firm* — Greer, Burns & Crain, Ltd.

(57) ABSTRACT

A method for controlling an apparatus for treating blood outside the human body, with a view to improving the operation of the apparatus, the apparatus including a semi-permeable membrane carrying out an exchange of solutes, referred to as dialysis, and of liquid, referred to as ultrafiltration, with the blood, the method including at least one iteration of the following steps: determination of a so-called instantaneous value, of an ultrafiltration coefficient corresponding to the ratio of an ultrafiltration flow rate to a difference in pressure, the so-called transmembrane pressure, on either side of the semi-permeable membrane, comparison of the instantaneous value with at least one previously determined characteristic value; and control of the treatment apparatus to reach a maximum value of the ultrafiltration coefficient, the control including a variation of the ultrafiltration flow rate up to a value corresponding to the maximum value of the ultrafiltration coefficient.

11 Claims, 3 Drawing Sheets

APPARATUS FOR EXTRACORPOREAL BLOOD TREATMENT AND METHOD FOR MANAGING SUCH AN APPARATUS

BACKGROUND

The invention relates to a method for managing an apparatus for treating blood outside a body. It also relates to a system implementing this method.

The invention relates more particularly to a method for managing an apparatus for treating blood outside a body with a view to removing liquid and solutes present in the blood. Such a method is more commonly called haemodialysis.

At present, several types of haemodialysis are known, carried out with apparatuses, called dialysis generators, comprising a filter, called a dialyzer, in which an exchange of solutes and liquids is carried out through a semi-permeable membrane.

In so-called "pure ultrafiltration" methods, the liquid to be removed is taken from the blood by pressure gradient and the solutes to be removed are transported by convection with the liquid.

In other haemodialysis methods, a fluid of a predetermined composition is introduced into the non-blood compartment of the dialyzer. The removal of the liquids from the blood through the semi-permeable membrane occurs by pressure gradient. The exchange of solutes through the membrane is achieved mainly by diffusion due to the concentration gradient of the solutes. Depending on the pressures and the porosity of the membrane various exchanges of water and solutes can take place.

In haemodiafiltration, the exchanges of solutes take place by diffusion and by convection. An additional quantity of liquid is removed by ultrafiltration. A substitution liquid is infused into the blood to compensate for the additional quantity of liquid removed.

All these types of haemodialysis allow the removal of an excess of liquid from the blood treated. The total quantity of liquid removed from the start to the end of the treatment (weight loss) is one of the most important parameters in the treatment, and it is generally fixed at the start of the treatment as a target.

Another important parameter is the total treatment time. The quantity of liquid removed from the blood treated per unit of time is known by the name of weight loss rate. Generally, the weight loss rate is fixed at a constant value or a predefined profile.

In haemodiafiltration, the quantity of liquid infused per unit of time is the infusion rate. The ultrafiltration rate is determined as the sum of the weight loss rate and the infusion rate. The difference in pressure on either side of the membrane is called the transmembrane pressure (PTM).

The ratio of the hourly ultrafiltration rate to the transmembrane pressure is called the ultrafiltration coefficient (KUF).

The manufacturers of treatment apparatuses give, for each type of dialyzer, an ultrafiltration coefficient value (KUF) measured in vitro with standard bovine blood. This value is generally taken as a constant in vivo. In vivo, for a given ultrafiltration flow rate (QINF), the adsorption into the membrane of proteins modifies the convection resistance and hence the transmembrane pressure (PTM). The ultrafiltration coefficient (KUF=QINF/PTM) is therefore not constant. It varies with the characteristics of the blood. The composition of the blood can vary during a session or be modified over several sessions. If the total ultrafiltered flow rate is greatly increased, as is the case in haemodiafiltration, the transmembrane pressure increases. A maximum flow rate value can be reached. This is the plateau where an increase in the transmembrane pressure (PTM) does not result in an increase in flow rate (dQuf/dPTM=0).

This maximum value of the total ultrafiltered flow rate is generally sought as a target value where convection resistance is significant. The weight loss results in an increase in the haematocrit during a session which can lead to haemoconcentration and the saturation of the membrane by proteins, resulting in transmembrane pressure alarms. The removal of toxins, in particular of high molecular weight, under these conditions diminishes. As the PTM increases, the ultrafiltration coefficient (KUF) decreases.

A purpose of the invention is to remedy these drawbacks.

Another purpose of the invention is to propose a method for managing an apparatus for treating blood outside a body making it possible to improve the operation and the yield of the treatment apparatus.

Another purpose of the invention is to provide an apparatus for treating blood outside a body having a better yield than the apparatuses known at present.

SUMMARY

The invention makes it possible to achieve the abovementioned aims by a method for managing apparatus for treating blood outside the human body, with a view to improving the operation of said apparatus, said apparatus comprising a semi-permeable membrane carrying out an exchange of solutes, referred to as dialysis, and of liquid, referred to as ultrafiltration, with the blood, said method comprising at least one iteration of the following steps:

determination of a so-called instantaneous value, of an ultrafiltration coefficient, said coefficient corresponding to the ratio of an ultrafiltration flow rate to a difference in pressure, the so-called transmembrane pressure, on either side of said semi-permeable membrane, comparison of said instantaneous value with at least one previously determined characteristic value; and depending on said comparison, control of said treatment apparatus so as to reach a maximum value of said ultrafiltration coefficient, said control comprising a variation of the ultrafiltration flow rate up to a value corresponding to said maximum value of said ultrafiltration coefficient.

The removal of uraemic toxins from the blood by dialysis depends on the hydraulic and diffusive permeability of the semi-permeable membrane. During a treatment session, for a constant ultrafiltration flow rate, the adsorption into the membrane of proteins increases the convection resistance. The hydraulic permeability is modified. The hydraulic permeability is measured by determination of the ultrafiltration coefficient (KUF) which is equal to the ratio of the ultrafiltration flow rate in mL/h to the transmembrane pressure (PTM) in mmHg.

In fact, studies carried out by the applicant(s) show that the ultrafiltration coefficient varies in particular with the ultrafiltration flow rate. Its variation curve is not a plateau but a parabola. The maximum KUF value (KUF max) corresponds to the best convection flow rate with respect to the pressure stress. This is the optimum hydraulic permeability value for the membrane. This value which is obtained during a session takes account of the treatment characteristics: blood composition, flow rates, type of membrane, surface area etc.

The invention makes it possible to determine the optimum ultrafiltration coefficient for using a dialysis apparatus in its optimum rheological state.

Advantageously, the method according to the invention allows the best, not the maximum, use of a dialysis apparatus. In fact, the yield of a dialysis apparatus is optimum when the ultrafiltration coefficient is maximum, which corresponds to an ultrafiltration rate better than those obtained at present for a lower transmembrane pressure stress. This is a value which makes it possible to use the dialysis apparatus in its optimum rheological state.

Advantageously, the step of determination of the ultrafiltration coefficient can comprise at least one iteration of the following steps:
  measurement of the transmembrane pressure,
  calculation of the ultrafiltration flow rate achieved by the semi-permeable membrane, and
  calculation of the ultrafiltration coefficient value by dividing said ultrafiltration flow rate by said transmembrane pressure.

During the comparison step, the previously determined characteristic value or values can comprise:
  either values provided by the manufacturer of the treatment apparatus,
  or values determined during a previous iteration or during one or more previous treatment sessions.

Thus, the instantaneous ultrafiltration coefficient value can be compared to one or more values which are:
  either provided by the manufacturer of the treatment apparatus,
  or determined during one or more previous iterations or treatment sessions.

According to an embodiment, the maximum ultrafiltration coefficient value can be measured during the treatment session in progress by determination of the variation of said ultrafiltration coefficient as a function of the ultrafiltration flow rate, said determination comprising several iterations of the following steps:
  variation of the ultrafiltration flow rate
  measurement of the transmembrane pressure obtained for this ultrafiltration flow rate,
  calculation of the ultrafiltration coefficient value by dividing said ultrafiltration flow rate by said transmembrane pressure, and
  storage of said ultrafiltration coefficient calculated in association with the ultrafiltration flow rate;

In this embodiment, the method according to the invention comprises a first iteration during which a first value $KUF_0$ of the ultrafiltration coefficient is determined after measurement of the transmembrane pressure. This value is stored in memory. Then during a second iteration, the ultrafiltration flow rate is modified and a new value $KUF_1$ of the ultrafiltration coefficient is determined after measurement of the transmembrane pressure. If $KUF_1 > KUF_0$ then $KUF_1$ is stored in memory and so on. The series of iterations is stopped when $KUF_k > KUF_{k+1}$ is obtained. The optimum ultrafiltration flow rate is that which corresponds to the ultrafiltration coefficient $KUF_k$. In this embodiment, the instantaneous ultrafiltration coefficient value is compared to an ultrafiltration value determined during the previous iteration. As indicated above the comparison can be carried out with respect to a value given by the manufacturer or determined during previous sessions.

The determination of the variation of the ultrafiltration coefficient can be carried out at any time during the blood treatment session. The determination of the variation can be carried out several times during a treatment session in order to optimize the yield of the treatment apparatus. It can either be carried out automatically, or be activated by manual intervention by an operator.

As stated above, the variation of the ultrafiltration coefficient as a function of the ultrafiltration flow rate takes place according to a parabolic curve. The optimum ultrafiltration flow rate is that for which the ultrafiltration coefficient is substantially equal to the value corresponding to the top of this parabolic curve.

According to another aspect of the invention, an apparatus for treating blood outside the human body is proposed, comprising a dialysis chamber comprising a semi-permeable membrane carrying out an exchange of solutes, referred to as dialysis, and of liquid, referred to as ultrafiltration, with the blood, said apparatus comprising:
  means of determination of a so-called instantaneous value of an ultrafiltration coefficient, said coefficient corresponding to the ratio of an ultrafiltration flow rate to a difference in pressure, the so-called transmembrane pressure, on either side of said semi-permeable membrane,
  means of variation of the ultrafiltration flow rate, and
  a control module of said means of variation of the ultrafiltration flow rate, as a function of a comparison of said instantaneous value to a so-called maximum value.

Advantageously, the means of determination of the instantaneous ultrafiltration coefficient value can comprise:
  sensors for measuring the transmembrane pressure, and more particularly several sensors arranged at each inlet and outlet of the dialysis chamber and measuring the pressure at each inlet and outlet of the dialysis chamber;
  means of determination of the ultrafiltration flow rate, and
  means of calculation of an ultrafiltration coefficient value by dividing said ultrafiltration flow rate by said transmembrane pressure.

Each of the sensors and the means of calculation can be connected to the control module.

The apparatus according to the invention can advantageously comprise storage means arranged for storing at least one ultrafiltration coefficient value for an ultrafiltration flow rate value.

Moreover, the control means can comprise means of execution of instructions stored in storage means, optionally incorporated into the control module, said instructions carrying out a calculation of the maximum ultrafiltration coefficient value during a treatment session in progress by determination of the variation of said ultrafiltration coefficient as a function of the ultrafiltration flow rate, said determination comprising several iterations of the following steps:
  variation of the ultrafiltration flow rate
  measurement of the transmembrane pressure obtained for this ultrafiltration flow rate,
  calculation of the ultrafiltration coefficient value by dividing said ultrafiltration flow rate by said transmembrane pressure, and
  storage, in the storage means, of said ultrafiltration coefficient calculated in association with the ultrafiltration flow rate;

Advantageously, manual activation means can be arranged for manual activation:
  of the determination of the instantaneous ultrafiltration coefficient value, and/or
  of the determination of the maximum ultrafiltration coefficient value during a treatment session in progress.

Thus, the operator can at any time and as often as necessary activate the determination of the instantaneous ultrafiltration coefficient value. If the ultrafiltration value is lower, by a predetermined value, than the maximum value of this coefficient then the control module can adjust the ultrafiltration flow rate in order to reach the maximum ultrafiltration coefficient value.

The apparatus according to the invention can be utilized for:
- treating blood outside the human body by pure ultrafiltration,
- treating blood outside the human body by haemodialysis, or
- treating blood outside the human body by haemodiafiltration.

Advantageously, the dialysis chamber is disposable.

BRIEF DESCRIPTION OF THE DRAWINGS

Other advantages and characteristics of the invention will become apparent on examination of the detailed description of a method of implementation which is in no way limitative, and the attached drawings in which.

DETAILED DESCRIPTION

Figure 1:
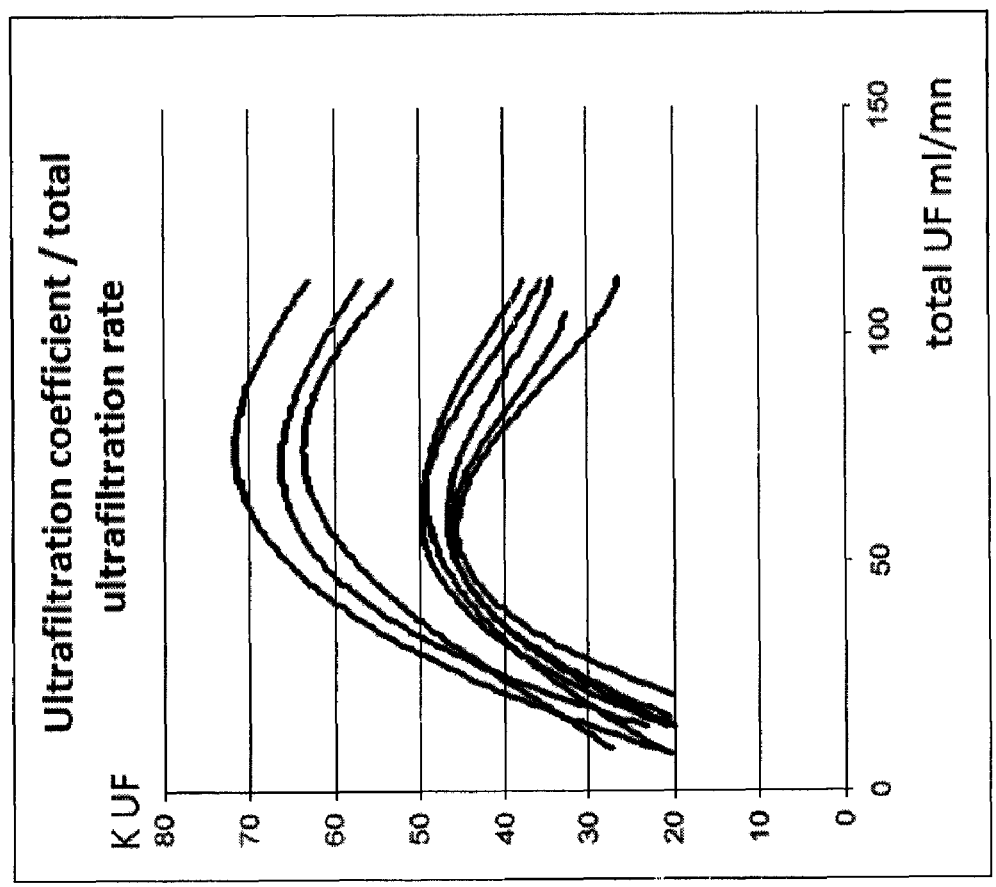
FIG. 1 illustrates examples of a variation profile of the ultrafiltration coefficient as a function of the ultrafiltration flow rate for the same type of dialyzer.

FIG. 1 shows several examples of variations of the ultrafiltration coefficient as a function of the ultrafiltration flow rate for the same type of dialyzer. As shown in FIG. 1, measurements show that the curve of the variation of the ultrafiltration coefficient KUF as a function of the ultrafiltration flow rate, increases, passes through a maximum then decreases. The general shape of the curve is a parabolic shape irrespective of the patient or the moment in time of the session. On the other hand the KUF values as well as the maximum values are different.

The ultrafiltration coefficient is therefore not a constant. It varies according to multiple factors including the characteristics of the membrane, the surface area, the blood composition or the flow rates. This is a new treatment parameter.

The monitoring of the ultrafiltration coefficient during the treatment makes it possible to control the working conditions of the ultrafiltration apparatus and to monitor, during the treatment, the two variables in the filter, the performance and the variations of the characteristics of the patient's blood in order to improve the yield of the semi-permeable membrane used to purify the patient's blood in a given situation.

Figure 2:
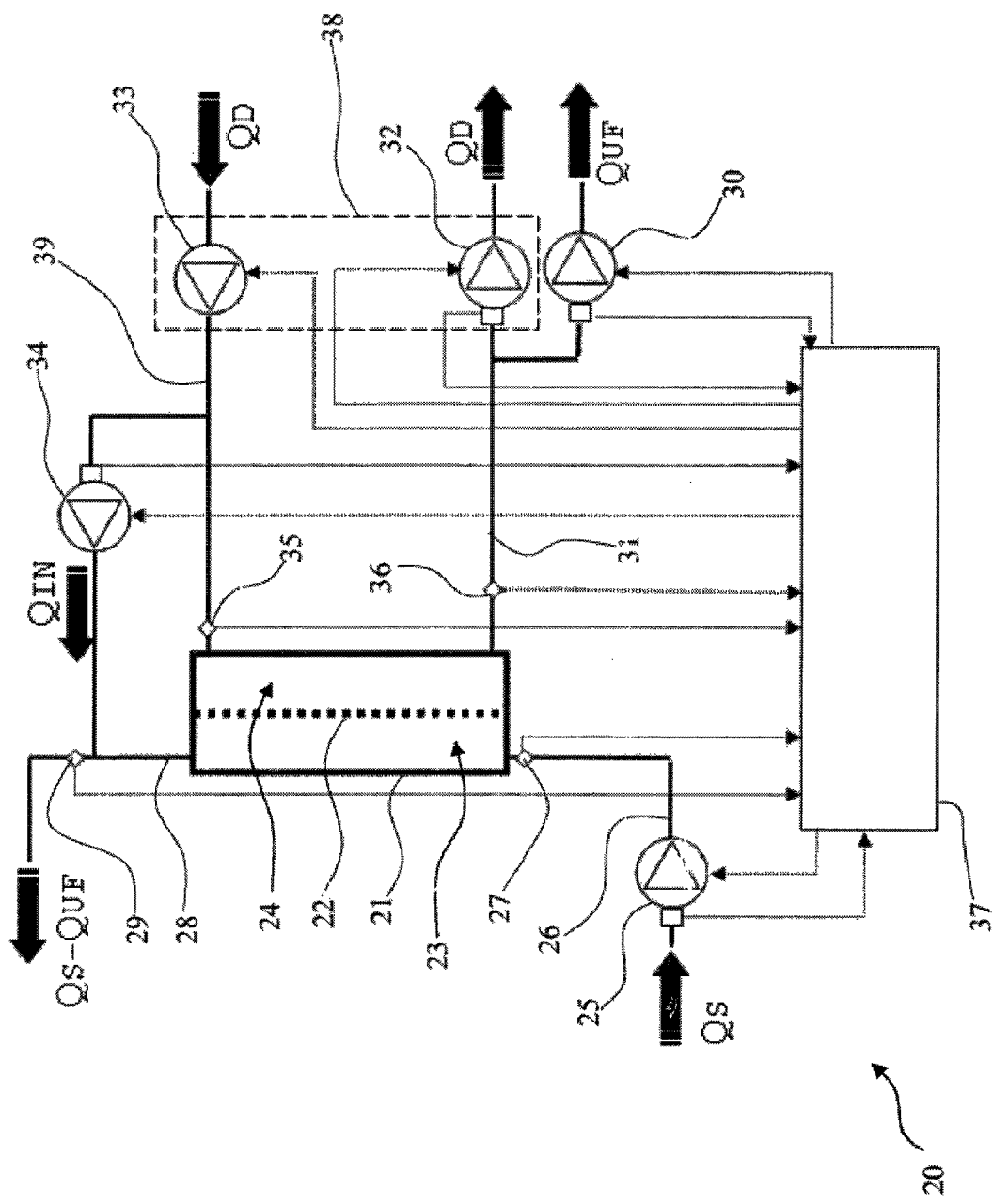
FIG. 2 is a diagrammatic representation of an apparatus which can be utilized for a pure ultrafiltration, haemodialysis or haemodiafiltration treatment.

We shall now describe, with reference to FIG. 2, an apparatus 20 for treating extracorporeal blood outside the body according to the invention. The apparatus 20 comprises a treatment chamber 21 comprising a semi-permeable membrane 22 which separates the internal volume of the treatment chamber 21 into two compartments: the compartment 23 which receives the blood to be treated and the compartment 24 which receives for example the dialysate. The apparatus 20 is suitable for carrying out pure ultrafiltration, haemodialysis or haemodiafiltration.

Case of a Pure Ultrafiltration Treatment

The treatment apparatus 20 also comprises a pump 25, for example of peristaltic type, arranged so as to circulate the patient's blood via the line 26 towards the treatment chamber 21, also called a dialyzer 21, at a regulated and controlled flow rate equal to $Q_S$.

The blood pressure is measured by a sensor 27 before the compartment 23 of the dialyzer 21. The blood is in contact with the semi-permeable membrane 22.

The treated blood is returned to the patient via the line 28. The pressure is measured by a sensor 29.

In pure ultrafiltration, a pump 30 situated on a line 31, connected to the compartment 24 of the dialyzer 21 operates at a flow rate precisely controlled by a device of known type and suitable for measuring an ultrafiltration flow rate equal to the weight loss rate $Q_{UF}$.

Pumps 32, 33 and 34 are occlusive and idle. A sensor 35 measures the pressure in this line 31 before the dialyzer 21.

The blood liquid is ultrafiltered through the semi-permeable membrane 22 towards the compartment 24 of the dialyzer and towards the pump 30. A sensor 36 measures the pressure.

The return flow of the dialyzer 21 towards the patient takes place at a flow rate equal to $Q_S - Q_{UF}$, $Q_{UF}$ being the weight loss rate.

A controller 37 receives pressure data from the sensors 27, 29, 35 and 36 and flow rate data from the pumps 25, 30, 32, 33, 34. The controller 37 is arranged so as to control the flow rate of the pumps 25, 30, 32, 33, 34.

This controller 37 calculates the transmembrane pressure PTM based on the values of the pressures measured at 4 points by the sensors 27, 29, and 36. The PTM is equal to the average of the pressures in the blood compartment 23 minus the average of the pressures in the dialysate compartment 24. In the absence of four sensors, the PTM can also be determined, but less precisely, by two sensors, one situated on the blood return line 28, and the other on the dialysate return line 31 or by three sensors with the third sensor positioned on the blood line at the inlet of the dialyzer, i.e. the line 26.

For the first measurement of the ultrafiltration coefficient, the controller 37 stops the ultrafiltration pump 30 and waits for the pressure measurements to stabilize, approximately 1 minute, then calculates the PTM and stores this value, equal to $PTM_0$ in storage means incorporated into the controller 37. It then increases the pump 30 to the flow rate value equal to a programmed weight loss, it waits for the measurements to stabilize, approximately 1 minute, then calculates the transmembrane pressure $PTM_i$. The calculated ultrafiltration coefficient value is equal to the weight loss rate $Q_{UF}$ divided by the value ($PTM_i - PTM_0$).

Regularly, during a session, the controller 37 will adjust the ultrafiltration coefficient value at the pump 3Q by stopping the ultrafiltration pump 30 for a stabilization period making it, possible to update the value $PTM_0$.

The ultrafiltration coefficient is displayed by the apparatus 20 on visualization means (not shown) and can be compared with values stored in memory, for example, characteristic values for the type of dialyzer or for the patient or values at the start of a session or values measured during this patient's previous sessions, in order to control inter-session or intra-session variations and initiate a procedure for improving the yield of the apparatus 20 or provide alert or alarm messages via the controller 37.

By pressing a button to start the control, the controller 37 stops the ultrafiltration pump 30 and waits for the pressure measurements to stabilize, approximately 1 minute, then calculates the PTM and stores this value, equal to $PTM_0$ in memory. The controller 37 then increases the flow rate of the ultrafiltration pump 30, by steps, up to the value $Q_{UFx}$ and for a predetermined stabilization period. At the end of each step, the PTM will be equal to $PTM_X$. The ultrafiltration coefficient is then determined with the formula:

$$\frac{Q_{UFx}}{PTM_x - PTM_0}$$

For the first step the ultrafiltration coefficient value is compared with characteristic values of different types of membranes stored in memory and with the patient's programmed weight loss.

Depending on the result, related to the type of membrane, different steps are provided by the calculator 37 provided that the remaining weight loss is greater than the sum of the weight losses produced for all the steps provided. The ultrafiltration flow rate and the PTM should be less than programmed limits, otherwise the optimum value of the ultrafiltration coefficient will be considered to be that obtained at the first limit.

The ultrafiltration coefficient value determined at the end of each step will be stored in memory and compared with the previous values. If this last value is less than the previous values of a certain pre-programmed value then there will be no additional step. The calculator 37 will calculate a trend line of the values and will adjust the flow rate of the ultrafiltration pump 30 in order to obtain the maximum clearance.

The calculator 37 will produce a signal indicating that the optimum value has been reached.

A confirmation of the flow rate value of the ultrafiltration pump 30 is requested by the calculator 37. If the value is confirmed, the ultrafiltration pump 30 is maintained at this value for the period provided or stopped when the weight loss provided is reached. The ultrafiltration coefficient will be continuously calculated. Regularly, during a session, the controller 37 will adjust the value by stopping the ultrafiltration pump 30 for a stabilization period making it possible to update the value $PTM_0$.

If the value is not confirmed, the ultrafiltration pump 30 will be maintained at the programmed weight loss value with respect to the dialysis time.

The treatment apparatus 20 also makes it possible to carry out a haemodialysis treatment.

Case of Haemodialysis Treatment

The blood circuit is unchanged with respect to pure ultrafiltration.

The pumps 32 and 33 allow the circulation of the dialysate into the dialyzer 21 and more precisely into the compartment 24 of the dialyzer 21. The dialysate passes through the semipermeable membrane 22 towards the compartment 23 of the dialyzer 21. The flow rate is equal to $Q_D$. Return from the dialyzer 21 takes place via the line 31 at a flow rate equal to $Q_D$ increased by the weight loss rate.

The pressure sensors 35 and 36 allow the calculation of the PTM. The circulation of the dialysate is in general controlled by a volumetric equilibrium module 38 the feature of which is that the flow rate $Q_D$ leaving this module 38 is identical to that returning to it. The weight loss is achieved by the pump 30. The flow rate $Q_{UF}$ is equal to the weight loss rate.

Instead of the volumetric equilibrium module 38 the circulation of the dialysate can also be carried out by two pumps, one at the inlet of the dialyzer and the other at the outlet. The outlet pump having a flow rate $Q_D$ equal to that of the inlet pump increased by the weight loss rate $Q_{UF}$. A device of known type measures and precisely controls the flow rates.

The measurement of the ultrafiltration coefficient and its adjustment are carried out in a manner comparable to that described for pure ultrafiltration.

The treatment apparatus 20 can also be used for treating blood by haemodiafiltration.

Case of Haemodiafiltration Treatment

A liquid is continuously infused into the patient by the pump 34 at a flow rate controlled by a known device (not shown) such as weighing or ultrasonic control means. This liquid can be taken from sterile bags, or, under certain conditions of asepsis and liquid quality, from the dialysate circuit on the line 39. This latter technique is known as on-line haemodiafiltration.

The apparatus is in haemodialysis mode, the dialysate circulates in the dialyzer 21. Part of the dialysate is collected by the pump 34 at a flow rate $Q_{IN}$. The flow rate in the line 39 at the inlet of the dialyzer 21 is therefore equal to $Q_D - Q_{IN}$. The flow rate at the outlet of the dialyzer 21, in the line 31, is therefore equal to $Q_D + Q_{UF}$ since the machine is operating on the haemodialysis principle. A quantity of liquid at a flow rate equal to $Q_{IN}$ is therefore ultrafiltered from the blood in order to maintain the flow rate equal to $Q_D + Q_{UF}$ at the outlet of dialyzer 21. At the blood compartment, the flow rate of blood at the outlet of the dialyzer 21 is equal to $Q_S - Q_{UF} - Q_{IN}$. As the pump 34 infuses at a flow rate equal to $Q_{IN}$, the flow rate of the blood returning to the patient is therefore equal to $Q_S - Q_{UF}$, i.e. the flow rate identical to that of haemodialysis.

The infusion liquid can be injected at: the outlet of the blood line from the dialyzer, the line 28 (post-dilution), or at the inlet, the line 26 (pre-dilution).

This dialysis technique makes it possible to increase the ultrafiltration inside the dialyzer 21. The ultrafiltration rate of the membrane 22 is then equal to $Q_{IN} + Q_{UF}$. The ultrafiltration coefficient (KUF) is the ratio of the hourly ultrafiltration rate, thus in this case: $Q_{IN} + Q_{UF}$, and the transmembrane pressure.

For the first measurement of the ultrafiltration coefficient, the controller 37 stops the ultrafiltration pump 30 and the infusion pump 34. It waits for the pressure measurements to stabilize, approximately 1 minute, then calculates the PTM and stores this value, equal to $PTM_0$ in memory. It restarts the ultrafiltration pump 30 at the previous value then increases the infusion pump 34 to the value provided by the user and programmed at the start of the session, it waits for the measurements to stabilize, approximately 1 minute, then calculates the transmembrane pressure $PTM_i$. The ultrafiltration coefficient value calculated will be equal to the ultrafiltration rate $Q_{INi} + Q_{UF}$ divided by the value $(PTM_i - PTM_0)$.

Regularly, during a session, the controller 37 will adjust the value by stopping the ultrafiltration 30 and infusion 34 pumps for a stabilization period making it possible to update the value $PTM_0$.

The ultrafiltration coefficient is displayed by the machine on visualization means connected to the controller 37 and can be compared with values stored in memory, for example, characteristic values for the type of dialyzer or for the patient or starting values of a session or values obtained during previous sessions for this patient, in order to control the inter-session or intra-session variations and bring about an improvement in the operation of the apparatus 20 or the alert or alarm messages via the controller 37.

The optimum permeability conditions will be sought, in this case, by varying the flow rate of the infusion pump 34.

By pressing a button to start the control, the controller 37 stops the infusion 34 and ultrafiltration 30 pumps and waits for the pressure measurements to stabilize, approximately 1 minute, then calculates the PTM and stores this value, equal to $PTM_0$ in memory. It will then restart the ultrafiltration pump 30 at the programmed value, then increase the infusion pump 34, by steps of a value and a predetermined stabilization period. At the end of each step the ultrafiltration coefficient will be determined with the formula: $(Q_{INx} + Q_{UF})$ divided by the value $(PTM_x - PTM_0)$. The ultrafiltration flow rate and the PTM should be less than programmed limits, otherwise the optimum value of the ultrafiltration coefficient will be considered to be that obtained at the first limit. At the end of each step the ultrafiltration coefficient value will be stored in memory by the controller 37 and compared with the previous values stored in memory. If this last value is less than the previous values by a certain programmed value then there will be no additional step. The controller will calculate a trend line of the values as shown in FIG. 1 and will adjust the flow rate of the infusion pump 34 in order to obtain the maximum clearance.

The controller 37 will produce a signal indicating that the optimum value is reached.

A confirmation of the flow rate value of the ultrafiltration pump 30 is requested by the controller 37. If the value is confirmed, the infusion pump 34 will be maintained at this value. The ultrafiltration coefficient will be calculated continuously. Regularly, during a session, the calculator 37 will adjust the value by stopping the ultrafiltration pump 30 for a stabilization period making it possible to update the value $PTM_0$. During the session, the optimum value can be sought either manually, or by programming or as a result of a variation in the KUF measured within predefined limits. This makes it possible, for example, to avoid coagulation in the blood circuit.

If the flow rate value of the ultrafiltration pump 30 is not confirmed, the infusion pump 34 will be maintained at the programmed value.

The characteristics of the KUF/UF curve (shape and maximum) will make it possible to verify if the dialyzer 21 is suitable for the patient.

This curve is a characteristic of a patient, not only for a single treatment, but also over the course of their illness. Certain modifications of the composition of the blood can be detected by comparing the curve profiles in an historical analysis, for example last or previous sessions, in order to reduce complications by a possible preventive treatment.

Figure 3:
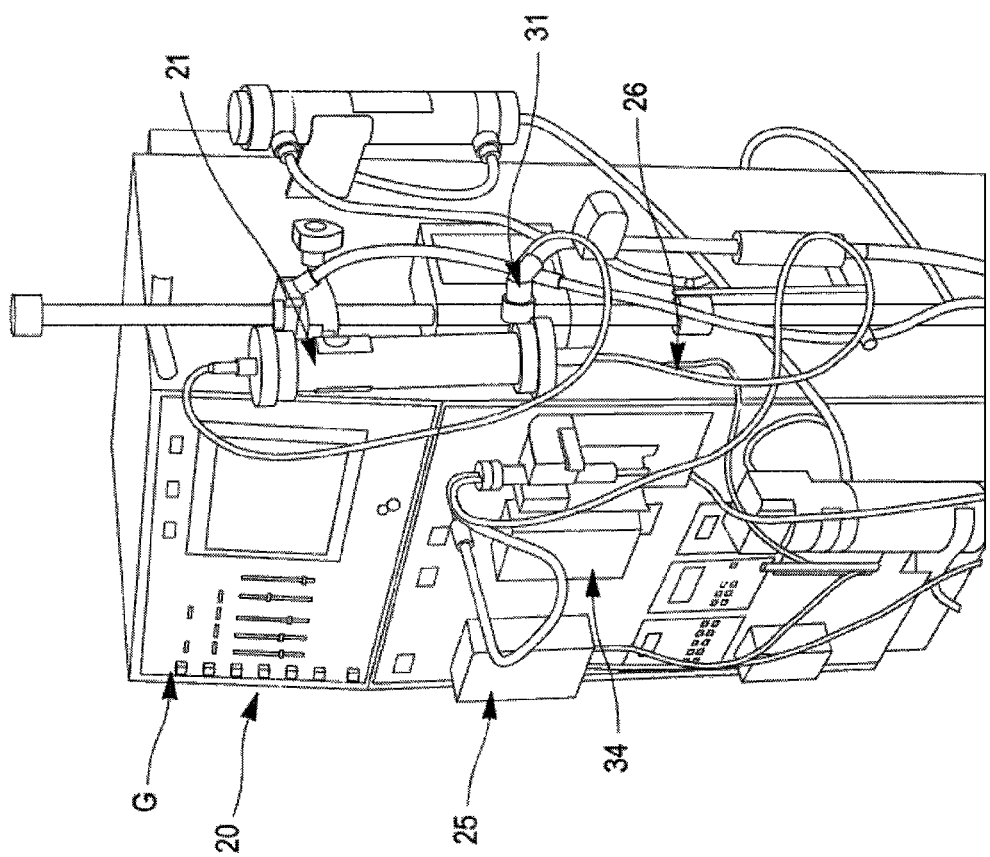
FIG. 3 is a diagrammatic representation of an example of an apparatus according to the invention.

FIG. 3 is a diagrammatic representation of an example of an apparatus 20 according to the invention. This figure shows the dialyzer 21 comprising the semi-permeable membrane, the pump 25 making it possible to circulate the blood in the line 26 as well as the infusion pump 34 and the line 31. Moreover, the apparatus 20 according to the invention also comprises a generator G for supplying energy to the different components of the apparatus 20.

The dialyzer 21 is situated outside the apparatus 20 according to the invention and can be changed easily by disconnecting the lines 26, 28, 31 and 39.

The invention makes it possible to improve the operation of an apparatus for extracorporeal blood treatment depending on the conditions relating to the patient at the start of the treatment.

Another advantage of the invention is that it can be adapted to the patient's situation and to the purification conditions which vary during a treatment.

Moreover, the apparatus according to the invention comprises a controller which can detect changes in parameters as a function of the composition of the blood and can therefore provide an historical analysis which is useful for improving the purification.

The apparatus according to the invention makes it possible to detect an abnormal rise in the haematocrit and therefore to prevent coagulation at the semi-permeable membrane.

Of course, the invention is not limited to the examples which have just been described and numerous adjustments can be made to these examples without exceeding the scope of the invention.

The invention claimed is:

1. A method for controlling an apparatus for treating blood outside the human body, with a view to improving the operation of said apparatus, said apparatus comprising a semi-permeable membrane carrying out an exchange of solutes, referred to as dialysis, and of liquid, referred to as ultrafiltration, with the blood, said method comprising at least one iteration of the following steps:
   determination of a so-called instantaneous value, of an ultrafiltration coefficient corresponding to the ratio of an ultrafiltration flow rate to a difference in pressure, the so-called transmembrane pressure, on either side of said semi-permeable membrane,
   comparison of said instantaneous value with at least one previously determined characteristic value; and
   control of said treatment apparatus so as to reach a maximum value of said ultrafiltration coefficient, said control comprising a variation of the ultrafiltration flow rate up to a value corresponding to said maximum value of said ultrafiltration coefficient.

2. The method according to claim 1, characterized in that the step of determination of the ultrafiltration coefficient comprises at least one iteration of the following steps:
   measurement of the transmembrane pressure,
   calculation of the ultrafiltration flow rate achieved by the semi-permeable membrane, and
   calculation of the ultrafiltration coefficient value by dividing said ultrafiltration flow rate by said transmembrane pressure.

3. The method according to claim 1, characterized in that the maximum value of the ultrafiltration coefficient is a value predetermined:
   by the manufacturer of the treatment apparatus, or
   during one or more previous treatment sessions.

4. The method according to claim 1, characterized in that the maximum ultrafiltration coefficient value is measured during the treatment session in progress by determination of the variation of said ultrafiltration coefficient as a function of the ultrafiltration flow rate, said determination comprising several iterations of the following steps:
   variation of the ultrafiltration flow rate
   measurement of the transmembrane pressure obtained for this ultrafiltration flow rate,
   calculation of the ultrafiltration coefficient value by dividing said ultrafiltration flow rate by said transmembrane pressure, and
   storage of said ultrafiltration coefficient calculated in association with the ultrafiltration flow rate.

5. The method according to claim 1, characterized in that it also comprises a determination of a hydraulic permeability of the semi-permeable membrane as a function of the ultrafiltration coefficient.

6. An apparatus for treating blood outside the human body comprising a dialysis chamber comprising a semi-permeable membrane carrying out an exchange of solutes, referred to as dialysis, and of liquid, referred to as ultrafiltration, with the blood, said apparatus comprising:
   means of determination of a so-called instantaneous value of an ultrafiltration coefficient corresponding to the ratio of an ultrafiltration flow rate to a difference in pressure, the so-called transmembrane pressure, on either side of said semi-permeable membrane,
   means of variation of the ultrafiltration flow rate, and
   means for controlling said means of variation of the ultrafiltration flow rate, as a function of a comparison of said instantaneous value to a so-called maximum value, so as to reach a maximum ultrafiltration coefficient.

7. The apparatus according to claim 6, characterized in that the means of determination of the instantaneous ultrafiltration coefficient value include:
- means of measurement of the transmembrane pressure,
- means of measurement of the ultrafiltration flow rate achieved by the semi-permeable membrane, and
- means of calculation of the ultrafiltration coefficient value from said ultrafiltration flow rate and said transmembrane pressure.

8. The apparatus according to claim 6, characterized in that it also comprises means for storing at least one ultrafiltration coefficient value for an ultrafiltration flow rate value.

9. The apparatus according to claim 6, characterized in that the means for controlling comprise means of execution of instructions stored in storage means, said instructions carrying out a calculation of the maximum ultrafiltration coefficient value during a treatment session in progress by determination of the variation of said ultrafiltration coefficient as a function of the ultrafiltration flow rate, said determination comprising at least one iteration of the following steps:

- variation of the ultrafiltration flow rate
- measurement of the transmembrane pressure obtained for this ultrafiltration flow rate,
- calculation of the ultrafiltration coefficient value by dividing said ultrafiltration flow rate by said transmembrane pressure, and
- storage of said ultrafiltration coefficient calculated in association with the ultrafiltration flow rate.

10. The apparatus according to claim 6, characterized in that it also comprises means for manual activation:
- of the determination of the instantaneous ultrafiltration coefficient value, and/or
- of the determination of the maximum ultrafiltration coefficient value during a treatment session in progress.

11. The apparatus according to claim 6, characterized in that the dialysis chamber is disposable.

* * * * *